United States Patent [19]

Slaunwhite, Jr.

[11] 4,358,435
[45] Nov. 9, 1982

[54] LIGAND COMPOSITIONS AND PROCESSES FOR THEIR MANUFACTURE AND THEIR USE IN RADIOIMMUNOASSAY

[75] Inventor: Wilson R. Slaunwhite, Jr., Snyder, N.Y.

[73] Assignee: The Research Foundation of State University of New York, Albany, N.Y.

[21] Appl. No.: 157,259

[22] Filed: Jun. 9, 1980

[51] Int. Cl.$^3$ .................... G01N 33/56; G01N 33/60; A61K 43/00; C07D 211/90
[52] U.S. Cl. ...................... 424/1; 23/230 B; 424/12; 548/351
[58] Field of Search .............. 424/1, 12; 23/230 B; 260/245.6; 548/351

[56] References Cited

U.S. PATENT DOCUMENTS

| | | | |
|---|---|---|---|
| 4,031,117 | 6/1977 | Rao | 424/12 X |
| 4,069,305 | 1/1978 | Polito et al. | 424/1 |
| 4,115,539 | 9/1978 | Eisenhardt, Jr. et al. | 424/12 X |
| 4,124,766 | 11/1978 | Paul et al. | 548/351 |
| 4,197,286 | 4/1980 | Rao | 424/12 X |
| 4,220,598 | 9/1980 | Hixson, Jr. et al. | 424/1 |
| 4,221,725 | 9/1980 | Bernstein et al. | 424/1 X |
| 4,230,621 | 10/1980 | Bernstein et al. | 424/1 X |
| 4,277,460 | 7/1981 | Kojima et al. | 424/12 X |

*Primary Examiner*—Christine M. Nucker
*Attorney, Agent, or Firm*—Michael L. Dunn

[57] ABSTRACT

A process for preparing a radioactive ligand by reacting an activated ester of the ligand with a primary amine containing a radioactive isotope.

An essentially pure composition having the formula:

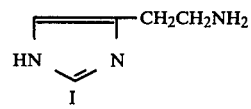

where I is $I^{125}$ or non-radioactive $I^{127}$.

A composition comprising a ligand connected by means of an amide linkage to the above essentially pure composition; and A process for radioimmunoassay using a ligand connected by means of an amide link to an essentially pure composition having the above formula where I is $I^{125}$.

18 Claims, 1 Drawing Figure

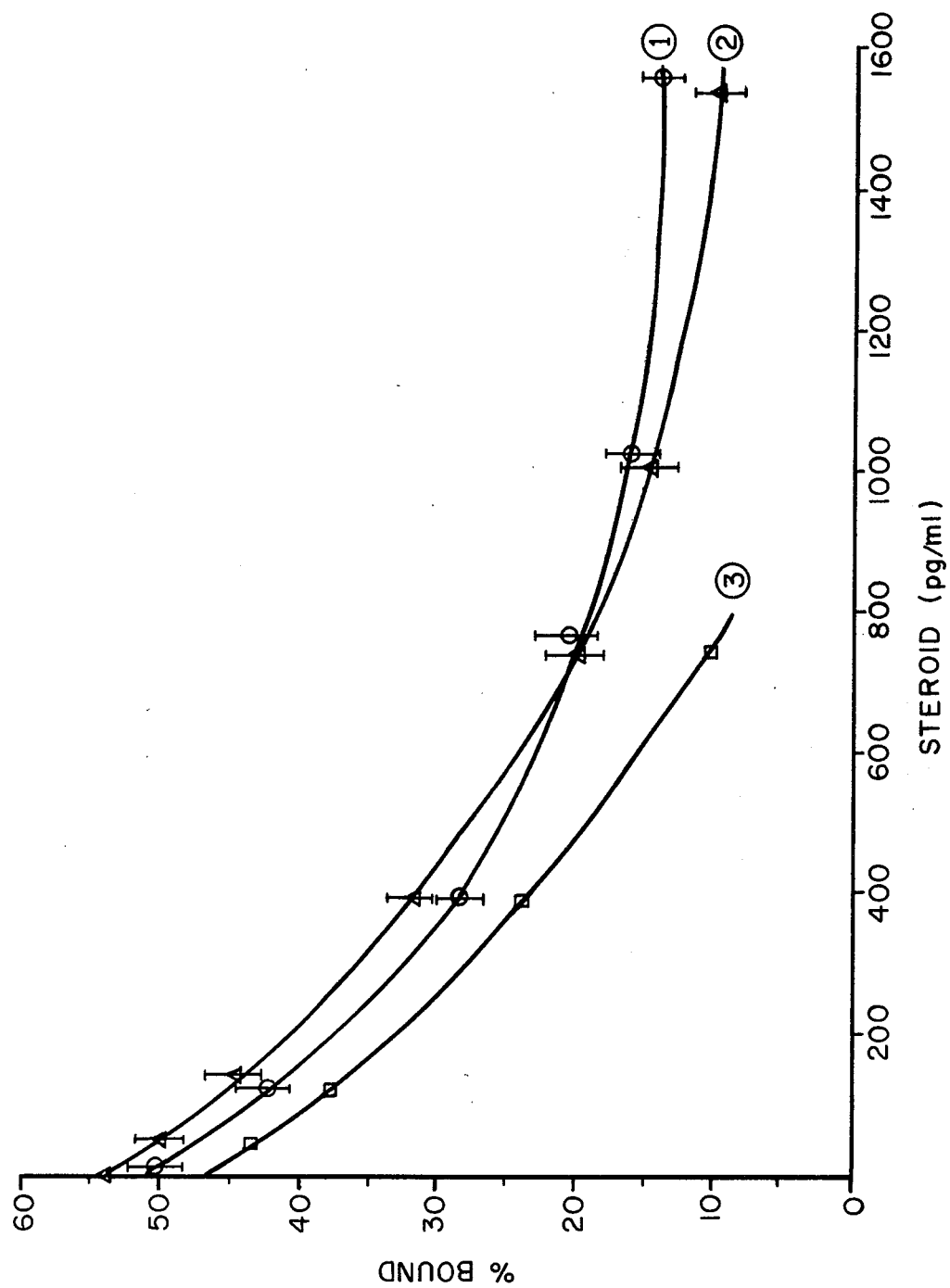

LIGAND COMPOSITIONS AND PROCESSES FOR THEIR MANUFACTURE AND THEIR USE IN RADIOIMMUNOASSAY

BACKGROUND OF THE INVENTION (A) Field of the Invention

This invention relates to analytical methods for measuring minute quantities of organic compositions and more particularly relates to the measurement of ligands by radioimmunoassay.

(B) History of the Prior Art

In the prior art, minute quantities of organic compositions were often measured by radioimmunoassay wherein an antibody is raised against the composition to be measured or in the case where the composition is not antigenic, such as the case of amino acid derivatives or steroids, an antibody is raised against the composition coupled to an inert protein as a hapten.

The antibody is then reacted with a known quantity of radioactively labeled composition which is then separated from excess free composition.

When a sample containing an unknown quantity of non-radioactive antigenic or hapten composition, i.e., ligand, is added to the antibody-radioactively labeled composition complex, the amount of radioactive composition that is complexed is reduced. By comparing the degree of reduction with that brought about by a known amount of non-radioactive composition, the concentration of the ligand composition in the unknown sample can be assessed.

While radioimmunoassay is an excellent method for analyzing organic compositions which can act as ligands (as antigens or as antigens when joined with an inert protein), there are nevertheless problems with its widespread application.

One of the most frequent methods used for radioimmunoassay in the prior art involves the use of radioactive hydrogen to tag the composition. Unfortunately, radioactive hydrogen produces weak beta rays which are difficult to measure and, in addition, introducing radioactive hydrogen into the ligand composition can not always be readily accomplished.

Recently it has been suggested that radioactive iodine ($I^{125}$) could be used to tag ligands. Unfortunately, the methods for introducing radioactive iodine into the ligand were not as easy as desired.

One suggestion was made by Nars and Hunter in the Journal of Endrocrinology xlvii, 1973, that certain hormones could be labeled with radioactive iodine by combining certain undefined radioactive iodine containing histamine compositions with the hormone ligand by utilizing a complex anhydride reaction process. This method was expanded by Cameron et al in articles appearing in Biochemical Society, Volume 1, Page 1115, 1973 and in the Journal of Steroid Biochemistry, Volume 5, Page 748, 1974.

Unfortunately, the method is not entirely satisfactory since the radioactively tagged histamine composition is not completely stable and has a short chemical shelf life thus creating variable results. Furthermore, reactivity with non-radioactive ligand was not as high as desired thus small changes in non-radioactive ligand are more difficult to detect. In addition, the complex anhydride reaction required to utilize the iodine tagged histamine composition by the Cameron et al references is difficult and cannot be readily be practiced by technicians.

BRIEF DESCRIPTION OF THE DRAWINGS

The drawing is a graph of percent of bound radioactive ligand against the concentration of non-radioactive ligand present in a system.

BRIEF DESCRIPTION OF THE INVENTION

In accordance with the invention, there is provided a radioactively tagged ligand which comprises a radioactively tagged primary amine connected to a ligand structure by means of an amide link. The primary amine preferably comprises histamine tagged with radioactive iodine ($I^{125}$). The composition of the invention can be readily prepared by reacting the radioactively tagged primary amine with an activated ester of the ligand. The activated ester group is any suitable group which can be displaced by a primary amine. Examples of such ester groups are those formed between carboxylic acids and N-hydroxysuccinimide or N-hydroxyphthalimide. The preferred activated esters, in accordance with the invention, are N-hydroxysuccinimide esters.

In accordance with the invention, an essentially pure composition having the formula:

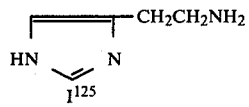

is reacted with an activated ester of the ligand to form a ligand connected with a radioactively tagged histamine group by means of an amide link. The resulting radioactively tagged ligand is chemically more stable than prior art ligands tagged with histamine. Furthermore, the composition is much more readily prepared in accordance with the process of the invention than was previously possible using prior art processes and reactivity with non-radioactive ligand is better than the reactivity of prior art radioactive ligands containing histamine structures.

The invention further comprises an essentially pure composition having the formula:

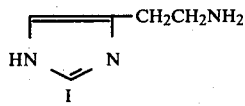

wherein the iodine atom is non-radioactive. This composition is suitable for use as a standard for chromatography and for use in reactions leading to the development of Scatchard plots to determine antibody affinity. The composition may also be suitable as an alkylating agent for attaching a histamine group to various organic compounds.

DETAILED DESCRIPTION OF THE INVENTION

In the prior art, ligands tagged with histamine containing $I^{125}$ were chemically unstable. Until the present invention, it was not recognized that the chemical instability was due to the lack of purity of a particular iodo histamine compound used to tag the ligand. Therefore, in accordance with the present invention, there is provided a new composition of matter which is an essentially pure composition having the formula:

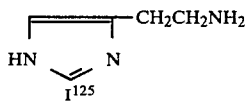

And, an essentially pure composition having the formula:

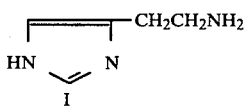

It has been unexpectedly found that the above particular histamine compositions ($I^{125}$-2-iodo histamine and 2-iodo histamine) show barely perceptible change within a sixty day period; whereas, certain other iodo histamines, in particular, 1,2,5-triiodohistamine and 2,5-diiodohistamine, whether or not radioactive iodine is used, are unstable. In the prior art, these compounds were present in the iodo histamine compositions used to tag ligands thus resulting in test compositions having composition properties which vary over undesirably short periods of time.

"Essentially pure", as used herein, means purity of 98% or greater and preferably purity of at least 99%.

In accordance with the present invention, it has been found that iodination of histamine proceeds rapidly at a pH of up to 8.4 to yield principally 2-iodohistamine which is the preferred iodohistamine for use in accordance with the present invention. In the iodination process, whether radioactive iodine is used or not, an excess of iodine is generally not used since substantial diiodination occurs, especially in basic systems. When additional purification is required, such purifications are easily accomplished by means known to those skilled in the art on a macro scale and when radioactive iodine containing compounds are used on a micro scale, the diiodo product can be easily isolated by a single thin layer chromatography process using silica gel in a solvent system of ethanol, ethyl ether and water at a ratio of 5:5:2.

The invention further comprises a process for the preparation of a radioactive ligand which comprises reacting an activated ester of the ligand with a primary amine containing a radioactive isotope.

The activated ester of the ligand is formed by reacting a carboxy containing ligand with a suitable hydroxy containing compound. In general, such reactions proceed readily by known means. Suitable hydroxy containing compounds are limited in number since the compound must readily form an ester with a carboxylic acid and the resulting ester must be readily subject to attack by a primary amine. Especially suitable hydroxy compounds are N-hydroxy compounds especially where the nitrogen is connected to one and preferably two carbonyl carbon atoms. Examples of such compounds are N-hydroxysuccinimide and N-hydroxyphthalimide.

The most preferred activated ester of the ligand is formed from the carboxy containing ligand and N-hydroxysuccinimide and has the formula:

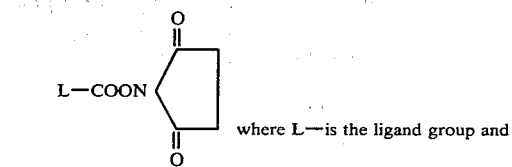

where L— is the ligand group and

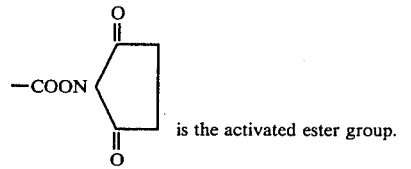

is the activated ester group.

The primary amine which is reacted with the activated ester of the ligand to form a radioactive ligand may be any suitable primary amine containing a radioactive element such as $I^{125}$, $H^3$, $I^{131}$ or $Se^{75}$.

In accordance with this invention, the preferred primary amine comprises a primary amine group connected to a radical containing an imidazole ring. The imidazole ring may be independent or fused with other rings such as with pyrimidine to form purine. The imidazole ring may be substituted or unsubstituted; provided that, the primary amine group must be connected directly or indirectly to the imidazole ring. The most preferred primary amine is $I^{125}$-2-iodohistamine. In general, an excess of activated ester is used in the reaction. The reaction proceeds readily at room temperature but is preferably carried out at lower temperature, e.g., 0° to 15° C. to better control the reaction.

The resulting radioactive ligand has the generic formula:

$$L-\underset{R}{CONH}$$

wherein L- is a ligand group and R- is an organic radical containing a radioactive isotope.

It is believed that the radioactive ligands resulting from the process of the invention are novel compositions when the radioactive isotope is $I^{125}$ attached to the 2 carbon atom between the nitrogen atoms in imidazole ring. The imidazole ring may be an independent ring structure or may be fused with other rings, such as pyrimidine to form purine. The primary amine nitrogen may be attached to any alkyl group within the R-radical.

A particularly suitable radioactive ligand manufactured in accordance with the process of the invention has the formula:

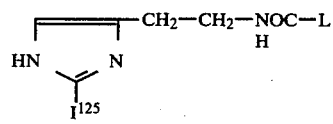

wherein -L is a ligand group.

The process of the invention may be used to form both known radioactive ligand compositions and the novel radioactive ligand compositions of the invention. Furthermore, the process of the invention may be used to manufacture the corresponding non-radioactive compositions for use as standards or as intermediates and the invention includes the novel corresponding non-radioactive compositions.

"Ligand", as used herein, is intended to include both antigens and haptens wherein a hapten is the portion of an antigen containing the grouping upon which the specificity depends.

Examples of ligands or ligand groups which form a part of compositions of the invention, which can be used to prepare radioactive ligands in accordance with the process of the invention and which can be assayed in accordance with the radioimmunoassay process of the invention include but are not limited to the following compositions. A carboxylic acid group must; however, be present and if not initially present, may be introduced by any suitable means.

Especially suitable ligands include steroid compounds which may be natural or synthetic or substituted. "Steroid compounds", as used herein, means any compound having a steroid ring structure which is usually aliphatic but may be provided with double bonds or an occasional aromatic ring.

Exemplary of such steroids include the estrogens including estradiol; progestins including progesterone; the androgens including testosterone; the glucocorticoids including cortisol; and the mineralocorticoids including aldosterone. In general, specific antibodies are formed against the steroids when the steroids are used in the form of haptens, i.e., connected with polypeptide.

Other ligands which may be used or analyzed in accordance with the present invention are amino acids and low molecular weight polypeptides and derivatives. "Low molecular weight", as used herein, generally means having a molecular weight of less than about 6,000 and preferably less than about 4,000. Examples of such polypeptides are polypeptide hormones including vasopressin (ADH), calcitonin, glucagon, secretin, gastrin, most releasing hormones including growth hormone releasing hormone, luteinizing hormone releasing hormone, follicle stimulating hormone releasing hormone and thyroid stimulating hormone releasing hormone; oxytocin; angiotensins and angiotensinogens and melanophore stimulating hormone ($\alpha$MSH) and perhaps insulin and adrenocorticotrophis hormone (ACTH). Before reaction with radioactive ligand, the amino groups of an amino acid or polypeptide should be blocked, i.e., with maleic anhydride. The amino groups can then be regenerated with mild acid, e.g., pH 3.

Also included as suitable ligands are the fatty acid hormones, such as prostacyclins and thromboxanes including the following prostaglandins: $PGE_1$; $PGF_1$; $PGE_2$; $PGF_{2\alpha}$.

Also included are the cyclic nucleotides, such as cyclic adenosine-3′,5′-monophosphate (cAMP) and guanosinemonophosphate (cGMP).

Other ligands which may be used are drugs used for medical treatment, such as analgesics including phenobarbitone and other barbiturates, acetaminophen, meperidine and aspirin; antimicrobials including sulfa drugs, such as sulfadiazine, sulfanilamide, sulfamethoxazole and antibiotics including penicillin, tetracycline, and oxytetracycline and tranquilizers such as chlorpromazine.

The following examples serve to illustrate and not limit the compositions and processes of the present invention. Unless otherwise indicated, all parts and percentages are by weight.

EXAMPLE 1

Preparation of 2-iodohistamine and 2,5-diiodohistamine

Four grams (21.72 moles) of histamine dihydrochloride in a minimum volume of water was adjusted to pH 7.5 with sodium hydroxide (concentrated solution). To this mixture was added drop by drop 21 ml of 0.1 M iodine solution in ethyl alcohol over a period of about 1.5 hours; the reaction was continued for an additional two hours. The mixture was then concentrated on a lyophylizer, and the concentrate was passed through a P-2 column (1.8 cm ID×30 cm) equilibrated with water:alcohol (3:1) collecting about 25 drops of eluting solvent in each of 33 tubes. Thin layer chromatography (TLC) of an aliquot from each tube revealed the composition of the eluate. Tube numbers 10–25 and 28–33 were pooled, the first fraction being 2,5-diiodohistamine and the second fraction 2-iodohistamine. The solvent from each fraction was evaporated to give a brown compound which was treated with charcoal and the product crystallized from ethanol/water acidified with hydrochloric acid.

The structure of the 2-iodohistamine was verified by NMR and microanalysis and the structure of the 2,5-iodohistamine was confirmed by microanalysis.

EXAMPLE 2

Preparation of Iodine-125 2-iodohistamine

Five nanomoles (10 $\mu$l) of a 5.5 mg/dl stock solution of histamine in phosphate buffer was iodinated with 25 $\mu$l (500 $\mu$Ci, ca. 0.25 nmole) of iodine-125 in buffer; 40 $\mu$g of chloramine T (10 $\mu$l of an aqueous solution containing 4 mg/ml) was used as the oxidizing agent; the iodination was carried out at 4° C. and stopped after 2 min. by the addition of 75 $\mu$g of sodium metabisulfite (10 $\mu$l from a stock aqueous solution containing 7.5 mg/ml).

The resulting $I^{125}$ 2-iodohistamine was purified and identified by TLC ($R_F$=0.484 for monoiodohistamine as determined from standard material prepared in accordance with Example 1). The identified TLC areas were scraped, eluted with 10 ml phosphate buffer and counted. The results indicate that optimum monoiodination is obtained after a reaction time of two to three minutes at which time, from about 70 to about 90% of the iodated histamine is monoiodohistamine. The sodium phosphate buffer used in the reaction is 0.1 molar buffer at pH 7.8. Chloramine-T is N-chloro-p-toluenesulfonamide. The thin layer chromatography plates were coated with silica gell containing a phosphor in a solvent system consisting of ethanol:ethyl ether:water at a volume ratio of 5:5:2.

EXAMPLE 3

Preparation of N-Hydroxysuccinimidyl Ester of Testosterone-3-(O-carboxymethyl) Oxime The above compound, also known as O-(2-oxo-3-(2′,5′-dioxypyrrol-1′-yl)-3-oxapropanyl) N-17beta-hydroxyandrost-4-en-3-ylidene hydroxylamine, was prepared as follows: N-hydroxysuccinimide, a compound well known in the art, was crystallized from ethyl acetate by addition of di-2-propyl ether. 1.15 g (10 mmoles) of this compound and 3.61 g (10 mmoles) of testosterone-3-(O-carboxymethyl) oxime were dissolved in a minimum volume (15 mL) of purified pyridine. The testosterone oxime can be prepared by several methods known to those skilled in the art. Examples of such methods are set forth in several publications including an article by Brenner et al in Steroids, Volume 22, page 775, 1973; Erlanger et al, Journal of Biological Chemistry, Volume 228, page 713, 1957 and Chen et al, Clinical Chemistry, Volume 17, page 581, 1971. The mixture was cooled to less than $-10°$ (the beaker containing the solution was placed in acetone-dry ice) at which point, 2.47 g (12 mmoles) of dicyclohexyl carbodiimide was added. The solution was stirred at $-10°$ for two hours, left at room temperature for ten hours and then treated with 0.12 mL of acetic acid to destroy excess dicyclohexyl carbodiimide. After one hour, the mixture was diluted with 5 mL of tetrahydrofuran; the precipitate consisting of dicyclohexyl urea was filtered off and washed with tetrahydrofuran. The combined filtrate and washings were evaporated to dryness under reduced pressure at 25°-30° to yield a dark, oily product which solidified upon addition of cold water. The product was dissolved in methanol and treated several times with neutral charcoal until a white solid was obtained. It was then crystallized twice from methanol and once from tetrahydrofuran/light petroleum ether. Yield of crude product was 82%.

EXAMPLE 4

Preparation of N-Hydroxysuccinimidyl Ester of Testosterone Hemisuccinate

The above compound, also known as 3-oxoandrost-4-en-17beta-yl N-2,5-dioxypyrrolyl succinate, was prepared as follows: Testosterone hemisuccinate (3.9 g or 10 mmoles) was esterified by the method described in Example 1., using 1.15 g (10 mmoles) of N-hydroxysuccinimide and 2.4 g (12 mmoles) of dicyclohexyl carbodiimide. The testosterone hemisuccinate was prepared in 85% yield by refluxing the testosterone steroid with succinic anhydride. The crude yield of the N-hydroxy succinimidyl ester of testosterone hemisuccinate was 80%.

EXAMPLE 5

Preparation of O-(2-iodohistaminylcarboxamidomethyl) testosterone oxime

The above compound, which is also known as O-2-oxo-5(2'-iodoimidazol-4'-yl)-3-azapentanyl N-17beta-hydroxyandrost-4-en-3-ylidene hydroxylamine was prepared as follows: To a solution of 0.62 g (2 mmoles) of 2 iodohistamine in a minimum volume (5 mL) of borate buffer, pH 8.0, was added 0.92 g (2 mmoles) of the N-hydroxysuccinimide ester of testosterone-3-O-carboxy-methyloxime, of Example 3., in 10 mL of tetrahydrofuran. The mixture was stirred at 4° for two hours after which it was poured into cold water. (A crystalline byproduct was identified as testosterone-3-O-carboxymethyloxime by its melting point and $R_f$). The mother liquor of the mixture, after filtering off the byproduct, was evaporated and the amorphous compound obtained was treated with charcoal until a white product was obtained; this compound crystallized from methanol. Crude yield, 59%.

EXAMPLE 6

Preparation of Oxoandrostenyl-2-Iodohistaminylsuccinamate

This compound, also known as 3-oxoandrost-4-en-17beta-yl N-2-(2'-iodoimidazol-4'-yl)ethyl succinamate, was synthesized as in Example 5. above using 0.62 g (2 mmoles) of 2-iodohistamine and 0.98 g (2 mmoles) of N-hydroxysuccinimidyl ester of testerone hemisuccinate prepared in accordance with Example 4. The same methods of purification were used. The crude yield of desired product is 57%.

EXAMPLE 7

Reaction of $I^{125}$-2-Iodohistamine with Activated Esters

Fifty nanomoles (10 μL of a 5.0 mM ethanolic solution) of N-hydroxysuccinimidyl ester of testosterone-3-(O-carboxymethyl) oxime or testosterone hemisuccinate was added to a crude iodination mixture prepared essentially in accordance with Example 2 except for the use of sufficient reactant to obtain about 50 nanomoles of $I^{125}$-iodohistamine, and stirred for 30 minutes at 4° C.; the mixture was then chromatographed on a thin layer plate. After air drying for one hour; the plates were directly applied to X-ray film (Kodak RP, rapid processing film) by inserting them between two boards and covering them with aluminum foil. After 30 min. in the dark, the films were developed and the areas corresponding to the 2-iodohistamine derivatives were carefully scraped off and extracted with 10 mL methanol. The diiodohistamine derivatives were also located, scraped off and extracted with 10 mL methanol. These derivatives were stored at these concentrations in the cold room and diluted as needed at the time of radioimmunoassay.

EXAMPLE 8

Radioimmunoassay

Standard curves of the percent of radioactive ligand bound against the quantity of testosterone steroid present were developed by introducing a known quantity of radioactive ligand prepared in accordance with Example 7. into a 12×75 mm polyethylene tube to which a known quantity of antibody and a known quantity of testosterone was added. After standing overnight, the tube was placed in an ice water bath for 30 minutes and sufficient polyethylene glycol solution (30 g of Carbowax ®6000 PEG and 0.1 g $NaN_3$ in 100 mL of water) was added to precipitate bound ligand. The tube was then vortexed, held for 15 minutes and centrifuged and the supernatant, which contains the unbound fraction of radioactive testosterone ligand due to competition with free testosterone, was decanted and counted for radioactivity. Since a known quantity of radioactive ligand was added, the percentage of bound radioactive ligand can be determined by substracting (from 100) the percentage of unbound radioactive ligand which is determined by the counting.

The quantity of known testosterone is varied and percent binding is determined for various testosterone concentrations, thus developing a standard curve.

When an unknown quantity of testosterone is added to a known quantity of radioactive ligand and antibody, the number of counts in the unbound fraction enables the concentration of the unknown testosterone to be determined by reference to the standard curve.

Desirably, the standard curve is adjusted for nonspecific antibody binding to the ligand.

Standard curves developed in accordance with this example are shown in the drawing. The antiserum (antibody) used is an antibody developed against testosterone-3-(O-carboxymethyl) oxime which was produced in sheep and obtained from Research Plus Steroid Laboratories, Inc., Denville, New Jersey.

In general, each of the points on the standard curve was determined by placing the following compositions into each tube: 100 μL of a phosphosaline-gelatin (PS-G) buffer (prepared by adding 6.89 g of $NaH_2PO_4 \cdot H_2O$, 7.1 g of $Na_2HPO_4$, 8.6 g of NaCl, 1 g of $NaN_3$ and 1 g of unflavored gelatin into 1 liter of solution); 100 μL of non-specific bovine gammaglobulin, 100 μL of specific testosterone-3-(O-carboxymethyl) oxime antiserum which was diluted with the phosphosaline gelatin buffer to give 50 to 60% binding; 100 μL of radioactive ligand to give 0.1 pica moles of iodated ligand or 0.2 pica moles of tritium tagged ligand; and varying quantities of testosterone steroid.

Standard curve number 1 shows percent binding versus steroid concentration when tritium labeled testosterone is used as the radioactive ligand. Curve 2 is the standard curve resulting when O-(2-$I^{125}$ iodohistaminyl-carboxamidyl-methyl) testosterone oxime is used as the radioactive ligand and Curve 3 is the standard curve resulting when oxoandrostenyl-2-$I^{125}$-iodohistaminyl succinamate is used as the radioactive ligand.

As can be seen from the drawing, there is a good correlation between the iodohistamine ligands and the tritium labeled ligand.

The iodated histamine ligands, as previously discussed and demonstrated, can be easily prepared in accordance with the process of the invention and in addition are much more easily counted due to gamma emissions which do not result from tritium labeled ligands.

In addition, the specificity of the iodinated histamine testosterone ligands is at least as good as the tritium labeled testosterone ligand and in all but one case tested, the specificity of the iodated histamine testosterone ligand is better than the tritium labeled testosterone ligand. Furthermore, tests for assay sensitivity show that the ligand of the invention is very good and can be dramatically improved by derivatizing the ligand before assay.

What is claimed is:

1. An essentially pure composition having the formula:

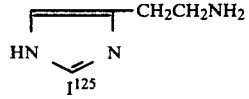

2. An essentially pure composition having the formula:

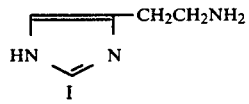

3. A composition comprising a carboxy containing ligand connected through the carboxy group by means of an amide linkage to the essentially pure composition of claim 1.

4. A composition comprising a carboxy containing ligand connected through the carboxy group by means of an amide linkage to the essentially pure composition of claim 2.

5. A composition comprising a polypeptide having a molecular weight of up to about 6,000 connected by means of an amide linkage to the essentially pure composition of claim 1.

6. A composition comprising an amino acid connected by means of an amide linkage to the essentially pure composition of claim 1.

7. A composition comprising a prostaglandin connected by means of an amide linkage to the essentially pure composition of claim 1.

8. A composition comprising a steroid connected by means of an amide linkage to the essentially pure composition of claim 1.

9. A composition comprising a cyclic nucleotide connected by means of an amide linkage to the essentially pure composition of claim 1.

10. In a process for measurement of minute quantities of a ligand by radioimmunoassay, the improvement which comprises using the composition of claim 3 as the radioactive ligand.

11. In a process for measurement of minute quantities of a ligand by radioimmunoassay, the improvement which comprises using the composition of claim 5 as the radioactive ligand.

12. In a process for measurement of minute quantities of a ligand by radioimmunoassay, the improvement which comprises using the composition of claim 6 as the radioactive ligand.

13. In a process for measurement of minute quantities of a ligand by radioimmunoassay, the improvement which comprises using the composition of claim 7 as the radioactive ligand.

14. In a process for measurement of minute quantities of a ligand by radioimmunoassay, the improvement which comprises using the composition of claim 8 as the radioactive ligand.

15. In a process for measurement of minute quantities of a ligand by radioimmunoassay, the improvement which comprises using the composition of claim 9 as the radioactive ligand.

16. A process for the preparation of a radioactive ligand which comprises reacting an activated ester of the ligand with a primary amine containing a radioactive isotope.

17. A process for the preparation of a radioactive ligand which comprises reacting an activated ester of the ligand with the composition of claim 1.

18. The process of claim 17 wherein the activated ester of the ligand has the formula:

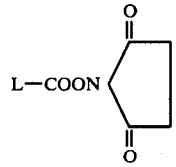 where L— is the ligand group and

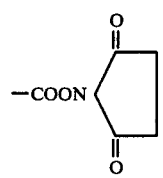 is the activated ester group.

* * * * *